US009118407B2

(12) United States Patent
Imran

(10) Patent No.: US 9,118,407 B2
(45) Date of Patent: Aug. 25, 2015

(54) SELF-PROPELLED BUOY FOR MONITORING UNDERWATER OBJECTS

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

(*) Notice: Subject to any disclaimer, the term of this patent is extended or adjusted under 35 U.S.C. 154(b) by 0 days.

(21) Appl. No.: 14/334,526

(22) Filed: Jul. 17, 2014

(65) Prior Publication Data
US 2015/0003192 A1 Jan. 1, 2015

Related U.S. Application Data

(63) Continuation of application No. 13/231,881, filed on Sep. 13, 2011, now Pat. No. 8,804,461.

(60) Provisional application No. 61/382,438, filed on Sep. 13, 2010, provisional application No. 61/384,612, filed on Sep. 20, 2010.

(51) Int. Cl.
*H04B 11/00* (2006.01)
*B63B 22/00* (2006.01)
(Continued)

(52) U.S. Cl.
CPC ............... *H04B 11/00* (2013.01); *B63B 22/00* (2013.01); *B63B 35/00* (2013.01); *B63B 35/44* (2013.01); *B63C 11/26* (2013.01); *B63H 25/04* (2013.01); *F03B 13/20* (2013.01); *G01S 3/80* (2013.01);
(Continued)

(58) Field of Classification Search
CPC ........... G01S 3/80; H04B 11/00; H04B 14/00
See application file for complete search history.

(56) References Cited

U.S. PATENT DOCUMENTS 3,369,516 A * 2/1968 Pierce ..................... 114/144 B
4,232,381 A 11/1980 Rennick et al.
(Continued)

FOREIGN PATENT DOCUMENTS

EP 2075189 A1 7/2009
FR 2655834 6/1991
(Continued)

OTHER PUBLICATIONS

EP Extended Search Report dated Jul. 17, 2014 in EP 11825827.6.
(Continued)

*Primary Examiner* — Luke Ratcliffe
*Assistant Examiner* — Hovhannes Baghdasaryan
(74) *Attorney, Agent, or Firm* — Mahamedi Paradice LLP

(57) ABSTRACT

Various embodiments of the invention provide a buoy and system for monitoring divers and other underwater objects. In many embodiments, the buoy has capabilities to monitor a diver, obtain position information about the diver and use that information to move itself to an effective range for continued monitoring. The buoy can connect and communicate with a communication device attached to a diver to communicate, position, biometric and other data. In one embodiment, the buoy comprises a propulsion system for propelling the buoy, an acoustic communication module for communicating with the diver and a propulsion controller for controlling the propulsion system to move to the effective range. Other embodiments provide a power generation system using a power generating buoy comprising an inertial weight, an energy converter and a connecting linkage. The system may comprise a single or multiple buoys and can include an electrical storage such as an electrical battery.

37 Claims, 7 Drawing Sheets

(51) Int. Cl.
*F03B 13/20* (2006.01)
*B63H 25/04* (2006.01)
*B63B 35/00* (2006.01)
*B63B 35/44* (2006.01)
*B63C 11/26* (2006.01)
*G01S 3/80* (2006.01)
*G05D 1/02* (2006.01)
*H04B 14/00* (2006.01)
*A61B 5/00* (2006.01)
*A61B 5/0205* (2006.01)

(52) U.S. Cl.
CPC .............. *G05D 1/0208* (2013.01); *H04B 14/00* (2013.01); *A61B 5/0002* (2013.01); *A61B 5/0205* (2013.01); *B63B 2022/006* (2013.01); *B63B 2035/006* (2013.01); *B63B 2035/007* (2013.01); *B63B 2035/4466* (2013.01); *Y02E 10/38* (2013.01)

(56) References Cited

U.S. PATENT DOCUMENTS

| | | | |
|---|---|---|---|
| 4,330,895 A | 5/1982 | Putman et al. | |
| 4,837,578 A | 6/1989 | Gammell | |
| 5,176,552 A | 1/1993 | Kuboyama et al. | |
| 5,331,602 A | 7/1994 | McLaren | |
| 5,577,942 A | 11/1996 | Juselis | |
| 5,664,636 A | 9/1997 | Ikuma et al. | |
| 5,712,447 A | 1/1998 | Hanson | |
| 5,717,657 A | 2/1998 | Ruffa | |
| 5,784,339 A | 7/1998 | Woodsum et al. | |
| 6,382,022 B1 | 5/2002 | Martinez et al. | |
| 6,402,690 B1 | 6/2002 | Rhee et al. | |
| 6,577,932 B1 | 6/2003 | Van Beurden et al. | |
| 6,854,410 B1 | 2/2005 | King et al. | |
| 6,856,578 B2 | 2/2005 | Magine et al. | |
| 7,642,919 B2 | 1/2010 | Leal et al. | |
| 2004/0090865 A1 | 5/2004 | Davies et al. | |
| 2004/0174259 A1 | 9/2004 | Peel et al. | |
| 2008/0037370 A1* | 2/2008 | Crowell | 367/127 |
| 2008/0162042 A1 | 7/2008 | Huber et al. | |
| 2009/0060353 A1 | 3/2009 | Saisan et al. | |
| 2009/0095208 A1 | 4/2009 | Cardoza et al. | |
| 2010/0091612 A1 | 4/2010 | Skrobanek et al. | |

FOREIGN PATENT DOCUMENTS

| | | |
|---|---|---|
| GB | 2390903 | 1/2004 |
| JP | 61-120980 A | 6/1986 |
| JP | 2006-021566 A | 1/2006 |
| WO | WO 2004/019776 | 3/2004 |

OTHER PUBLICATIONS

International Search Report and Written Opinion issued in International Application PCT/US2011/052429, dated Apr. 24, 2012.
International Search Report and Written Opinion issued in International Application PCT/US2011/051473, dated May 21, 2012.
First Examination report in European Application No. 11827392.9, mailed Apr. 16, 2014.

* cited by examiner

SELF-PROPELLED BUOY FOR MONITORING UNDERWATER OBJECTS

RELATED APPLICATIONS

This application is a Continuation of U.S. application Ser. No. 13/231,881, filed Sep. 13, 2011, titled "Self-Propelled Buoy for Monitoring Underwater Objects", which claims benefit of priority to U.S. Provisional Application No. 61/382,438, filed Sep. 13, 2010, titled "Self-Propelled Buoy For Monitoring Underwater Objects", and claims benefit of priority to U.S. Provisional Application No. 61/384,612, filed Sep. 20, 2010, titled "Device, System and Method for Monitoring and Communicating Biometric Data of a Diver", all of which are fully incorporated herein by reference in their entirety and for all purposes.

TECHNICAL FIELD

Embodiments described herein relate to a self-propelled buoy for monitoring underwater objects. More specifically, embodiments described herein relate to a self-propelled buoy for monitoring and communicating with divers and other underwater objects.

BRIEF DESCRIPTION

Various embodiments of the invention provide a buoy and system for monitoring divers and other underwater objects such as underwater robots, submarines, moorings and the like. In many embodiments, the buoy has capabilities of monitoring a diver and their position and propelling itself to be able to maintain its ability to monitor the diver. More particularly, embodiments of the buoy are configured to monitor a diver or other underwater object, obtain or derive position information on the diver and use that information for moving to an effective range for continuing to monitor the diver or other underwater object that is in water beneath the buoy.

In a first aspect, embodiments of the invention provide a self-propelled buoy for communication with a diver or other underwater object, comprising a propulsion system for propelling the buoy, an acoustic communication module and a propulsion controller. The propulsion system can include propellers, paddlewheels, jets or compressed gas and may be electric powered or powered by an internal combustion engine or combination of both in a highbred configuration. In preferred embodiments, the propulsion system comprises a propeller-driven system which may be powered by an internal combustion engine or an electric motor or a combination of both. Also, in various embodiments, the propulsion system can be arranged and configured to reduce acoustic interference with acoustic communication sent and received from the diver or other underwater object so that the communication module can send and receive communications from the diver (or other underwater object) while the propulsion system is on. Such embodiments can include for example, the use of acoustic shielding around all or a portion of the propulsion system particularly where it makes contact with the water, positioning of the propulsion system on an opposite side of the buoy and the use of low cavitation propellers for propeller driven embodiments.

The acoustic communication module is configured to at least receive acoustic communications from a communication device that is attached to the diver or objects located in water underneath the buoy. In many embodiments, the acoustic communication module is configured to transmit and receive and thus comprises a transmitter and a receiver that are configured to transmit and receive acoustic communications with a single or with multiple devices that are attached to single or multiple divers or other underwater objects. Each attached device has an identifier that enables it to be distinctly identifiable and detectable to the buoy. In one embodiment, the unique identification is an acoustic signature which may be included in an acoustic signal sent from the device to the buoy. Once the buoy is connected to a device, the device can transmit acoustic communications to the buoy. The acoustic communications can include information such as position information of the diver, information about the surrounding environment, biometric information relating to the diver, or information about the diver's equipment. In particular embodiments, the acoustic communication module can comprise a sonar device or other like device. Also in various embodiments, the acoustic communication module can include a filter to filter out acoustic interference from the propulsion system so that communications can be sent and received between the buoy and the diver (or other underwater object, e.g., a robot etc.) while the propulsion system is on. In other embodiments for reducing acoustic interference, the acoustic communications sent back and forth between the acoustic communications module and the diver's communication device can be processed for example, by frequency modulation, or frequency shifting to a higher or lower frequency which is not affected as much by propulsion sounds. A combination of both approaches may be used as well. Other processing methods known in the acoustic arts are also contemplated.

The propulsion controller is configured to identify or otherwise derive position information sent by the communication device of the underwater object, for example, based on analysis of the acoustic communications received by the acoustic communication module. The propulsion controller is further configured to output control information to control the buoy propulsion system so as to keep the buoy within a selected distance of the object. The controller may do so by controlling the speed and direction of the propulsion system to propel the buoy to a location within the desired distance of the object. In many embodiments, the controller comprises a microprocessor having one more software programs for controlling various aspects of the propulsion system (e.g., speed, acceleration, direction, movement pattern, etc.). However, in various embodiments, the propulsion controller may also comprise one or more of a standalone software program, a state device, an analogue-based controller, an ASIC, a servo controller or combinations thereof.

In another aspect, embodiments of the invention provide a system for monitoring biometric data of a diver using a buoy system. In one or more embodiments, the buoy can connect and communicate with a communication device attached to a diver. Once the buoy is connected to a communication device, the communication device can transmit acoustic communications to the buoy. In various embodiments, the communication device can be connected to a monitoring apparatus that is attached to the diver. The monitoring apparatus can measure and monitor various biometric information of the diver which is then sent to the diver attached communication device for communication as information to the buoy. Such biometric information can include for example, the diver's oxygen saturation level (or other blood gas such as nitrogen), heart and respiration rate, or blood pressure. The communication device can include a software module to convert the biometric information to acoustic communication. The acoustic communication can then be transmitted from the communication device to the buoy as described above.

In another aspect, various embodiments of the invention provide a power generation system using a power generating buoy. The power generation system can include a plurality of buoys or just one buoy. Each buoy comprises an energy converter, a water surface contact feature which typically comprises a flange (or flange shaped feature) and a weight. The weight is attached to the energy converter by means of a cable or other mechanical attachment means or it may be directly coupled to the energy converter. The energy converter may comprise one or more energy generating elements which generate energy from a force being exerted on those elements. The elements may be selected and arranged to generate energy without movement of the elements, e.g., a static configuration, or from movement of the elements, e.g., a dynamic configuration. An example of the former may include an energy converter comprising piezo-electric materials) while an example of the later may include a magnetic-based electrical generator.

In one or more embodiment, the mass of the weight, the length of the cable and the size of the flange are interrelated to maintain the buoy's balance so that it remains substantially on the surface of the water even with the passing of a wave. Though in other embodiments, these factors can be selected to maintain the all or portions of the buoy a selected distance below the waterline. As is explained in more detail herein, various embodiments of the power generation system generates power from the movement of waves resulting in up and downward movement of the cable which is then transferred to the energy converter. For dynamic configurations, the energy convertor can be configured to generate energy during both the upward and downward movement of the cable so that energy is generated during the entire period of an ocean or other wave.

In one embodiment, the energy generated from the above motion can then be stored in a local energy store in the buoy such as an electrical storage battery. In other embodiments, the power generation system can include an energy storage system to store the energy generated from a single buoy or multiple buoys. The storage system is coupled to the buoy or the plurality of buoys and can be connected by cables ashore or to a ship for purposes of power transfer. In one or more embodiments, the storage system can comprise a plurality of high capacity electrical storage batteries a preferred embodiment of which includes lead acid batteries (preferably marine-rated) though other electro chemistries described herein are equally applicable.

Further details of these and other embodiments and aspects of the invention are described more fully below, with reference to the attached drawing figures.

DETAILED DESCRIPTION

Figure 1:
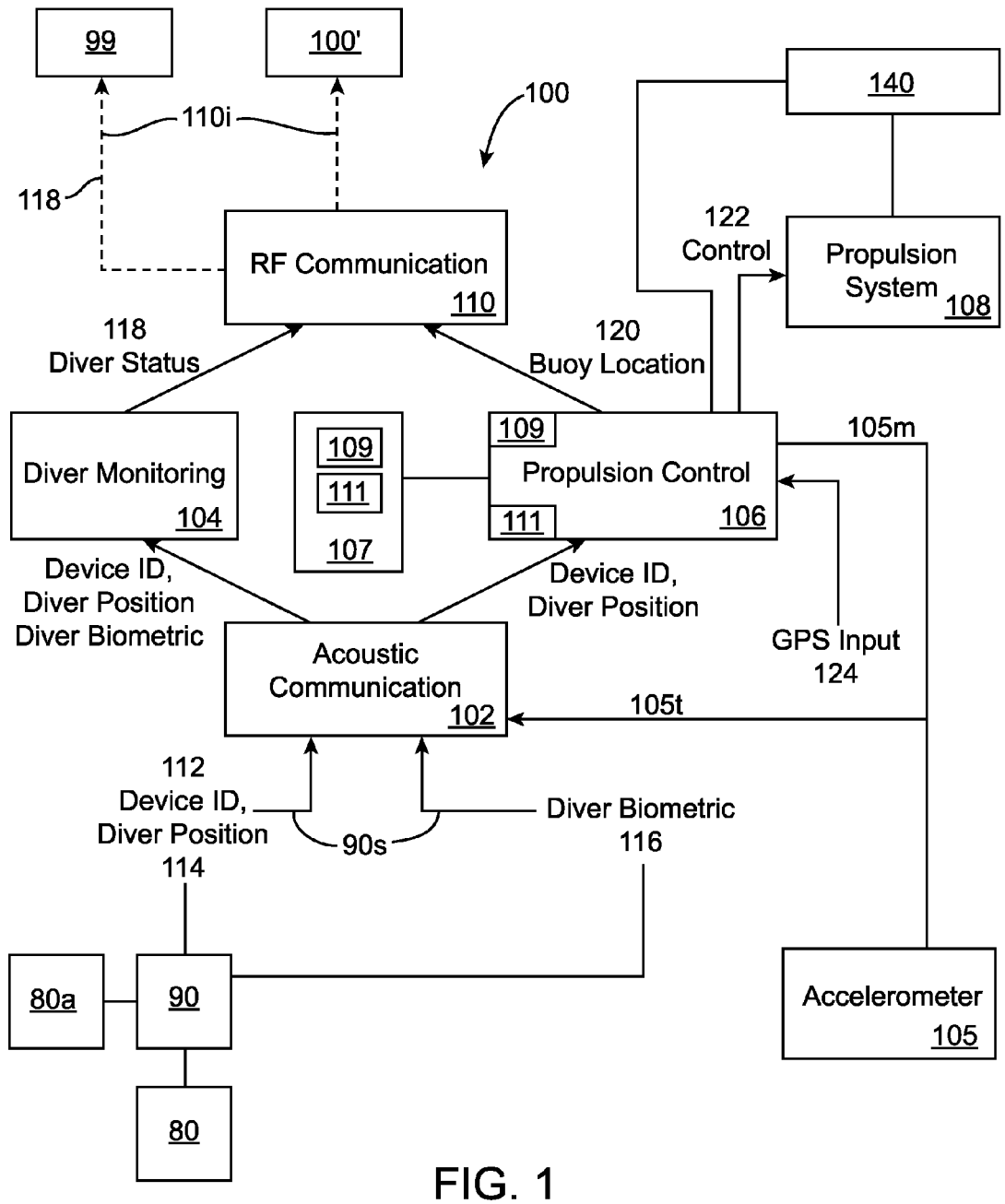
FIG. 1 is a block diagram illustrating the components of an embodiment of a self-propelled buoy.

Numerous embodiments are described herein for providing a buoy and system for monitoring divers and other underwater objects such as underwater robots, submarines, moorings and the like. According to some embodiments, a buoy is provided with capabilities of detecting a diver and their position, and for self-propelling itself to maintain its ability to monitor the diver. In particular, one or more embodiments provide a buoy that is capable of moving itself to an effective range for monitoring a diver that is swimming underneath.

As used herein, a buoy is a floatation device that can have various shapes or sizes. Also as used herein, the terms "acoustic" and "acoustical" are used interchangeably. According to some embodiments, the buoy includes a propulsion system that enables the buoy to move in a manner that maintains its proximity to underwater divers or other underwater object such as a robot, submarine, underwater cable, underwater pipeline, underwater drilling rig and components thereof. The propulsion system can include a combination of propellers, paddle wheels, pump jets, or other means for enabling movement in water. The propellers, paddle wheels and pump jets may be powered by one or more of electric motors, an internal combustion engine (e.g., in board or in board out board), compressed air/gas, or other power generation means known in the art. Also the propulsion system can be selected depending upon the particular underwater object to be tracked, its speed and expected depth. For example, higher speed systems can be used for tracking a submarine or other fast deep diving underwater object.

According to some embodiments, the buoy also includes an acoustic communication module for receiving acoustic communications from a device attached to a diver. The acoustic communication module, for example, can comprise a transmitter and a receiver that are configured to transmit and receive acoustic communications. In one embodiment, the acoustic communication module can be a sonar device. Furthermore, in one embodiment, the buoy can communicate with multiple devices that are attached to multiple divers. Each device has an identifier that enables it to be distinctly identifiable and detectable to the buoy. In one embodiment, the unique identification is an acoustic signature which may be included in an acoustic signal sent from the device to the buoy. Once the buoy is connected to a device, the device can transmit acoustic communications to the buoy. According to an embodiment, the acoustic communications can include information such as position information of the diver, information about the surrounding environment (e.g., temperature and depth), biometric information of the diver, or information about the diver's equipment. The position information can include for example, the absolute position of the diver in terms of latitude and longitude, the position of the diver relative to the position of the buoy, the absolute speed and direction of moment of the diver, and the speed and direction of movement of the diver relative to the buoy. The position information can also be derived from information contained in the acoustic communication, for example, using various acoustic processing methods known in the art for determining distance, depth and speed of an object such as various sonar methods or like methods.

In many embodiments, the buoy includes a propulsion controller that receives acoustic communications from the acoustic communication module. Based on the acoustic communications, the propulsion controller is configured to identify at least position information of a diver. The propulsion controller may also derive position information based on analysis of the acoustic communication, for example, using acoustically-based methods known in the art for determining one or more of distance, depth and speed such as various sonar methods. In one embodiment, the propulsion controller uses position information of the diver to output control information to control the propulsion system of the buoy. In this way, upon determining that the diver is moving out of the buoy's communication range, the propulsion controller can control the propulsion system in moving the buoy back within an effective communication range. The controller may do so by controlling the speed and direction of the propulsion system to propel the buoy to a location within the desired distance of the object. In many embodiments, the controller corresponds to a microprocessor having one more software programs for controlling various aspects of the propulsion system (e.g., speed, acceleration, direction, movement pattern, etc.). However, in various embodiments, the propulsion controller may also correspond to a standalone software program, a state device, an analogue-based controller, an ASIC, a servo controller or combinations thereof. In many embodiments, the controller includes servo control components to be able to control the speed and direction of the propulsion system using servo control mechanisms and methods known in the art.

In some embodiments, the buoy includes a radio frequency (RF) communication module that can transmit information from the buoy to another buoy or to a monitoring ship (e.g., a dive boat). The information transmitted can include data about the buoy and/or its surrounding environment, such as the buoy's location, currents, tide conditions, wind speeds, water temperature, or data about the diver, such as position information of the diver, biometric information of the diver, or information about the diver's equipment. In another embodiment, the RF communication module can also be configured to receive instructions from another buoy or a monitoring ship. The RF communication module can then relay these instructions to enable the buoy to respond accordingly.

In another aspect, embodiments of invention provide a system for monitoring biometric data of a diver using a buoy system. In one or more embodiments, the buoy can connect/link and communicate with a communication device attached to a diver. Once the buoy is connected to a communication device, the communication device can transmit acoustic communications to the buoy. In various embodiments, the communication device can be connected to a monitoring apparatus that is attached to the diver. The monitoring apparatus can measure and monitor various biometric information of the diver which is then sent to the diver attached communication device for communication to the buoy. Such biometric information can include for example, the diver's oxygen saturation level (or other blood gas such as nitrogen), heart and respiration rate, or blood pressure. The communication device can include a software module to convert the biometric information to acoustic communication. The acoustic communication can then be transmitted from the communication device to the buoy as described above.

In another aspect, various embodiments of the invention provide a power generation system using a power generating buoy. The power generation system can include a plurality of buoys or just one buoy. Each buoy comprises an energy converter, a water surface contact feature which typically comprises a flange (or flange shaped feature) and a weight. The weight is attached to the energy converter by means of a cable or other mechanical attachment means or it may be directly coupled to the energy converter. The energy converter may comprise one or more energy generating elements which generate energy from a force being exerted on those elements. The elements may be selected and arranged to generate energy without movement of the elements, e.g., a static configuration, or from movement of the elements, e.g., a dynamic configuration. An example of the former may include an energy converter comprising piezo-electric materials) while an example of the later may include a magnetic-based electrical generator.

In one or more embodiment, the mass of the weight, the length of the cable and the size of the flange are interrelated to maintain the buoy's balance so that it remains substantially on the surface of the water even with the passing of a wave (though in other embodiments, the factors can be selected to maintain all or portions of the buoy a selected depth below the waterline). When the buoy encounters waves, it moves up and down with the passing of each wave. As the buoy moves upwards with a wave, the weight exerts a downward force on the cable and in dynamic configurations, actually pulls the cable downward away from the energy converter thereby producing movement of the energy converter elements. When the wave moves downward, the force is released and in dynamic configurations, the cable moves back upward. In this way, energy can be created from the pulling and/or other movement of the cable. For dynamic configurations, the energy convertor can be configured to generate energy during both the upward and downward movement of the cable so that energy is generated during the entire period of an ocean or other wave. In one embodiment, the energy generated from this motion can then be stored in a local energy store in the buoy such as an electrical storage battery. In another embodiment, the power generation system can include an energy storage system to store the energy generated from the buoy or multiple buoys.

The storage system is coupled to the buoy or the plurality of buoys and can be connected by cables ashore or to a ship for purposes of power transfer. In one or more embodiments, the storage system can comprise a plurality of high capacity electrical storage batteries which can include one or more of lead acid, nickel metal hydride or lithium ion chemistries. As an addition or alternative embodiment, various mechanical energy storage means may also be employed such as springs, and various pressure storage systems.

Figure 1A:
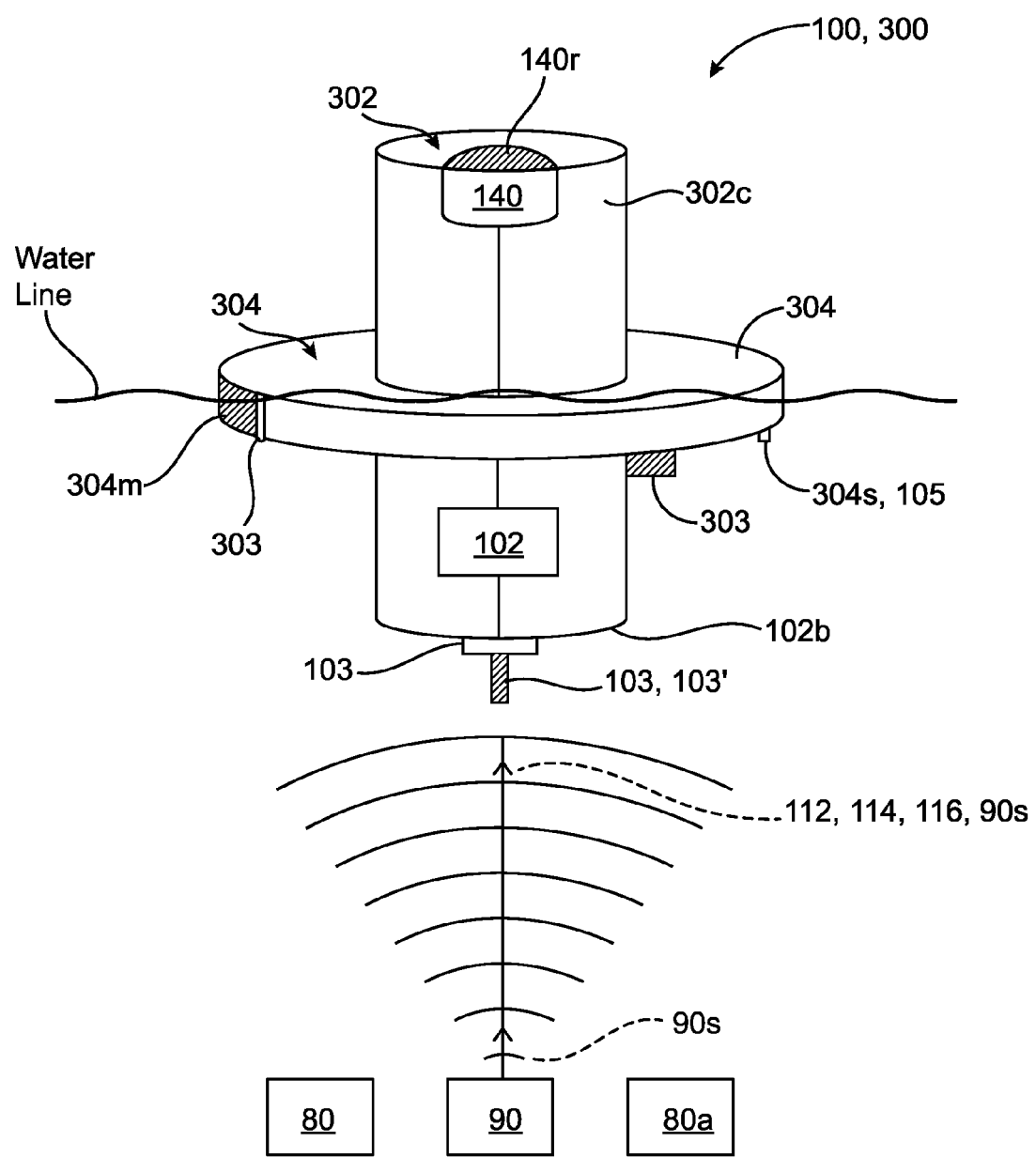
FIG. 1a illustrates the structure of an embodiment of a self-propelled buoy.
Figure 2:
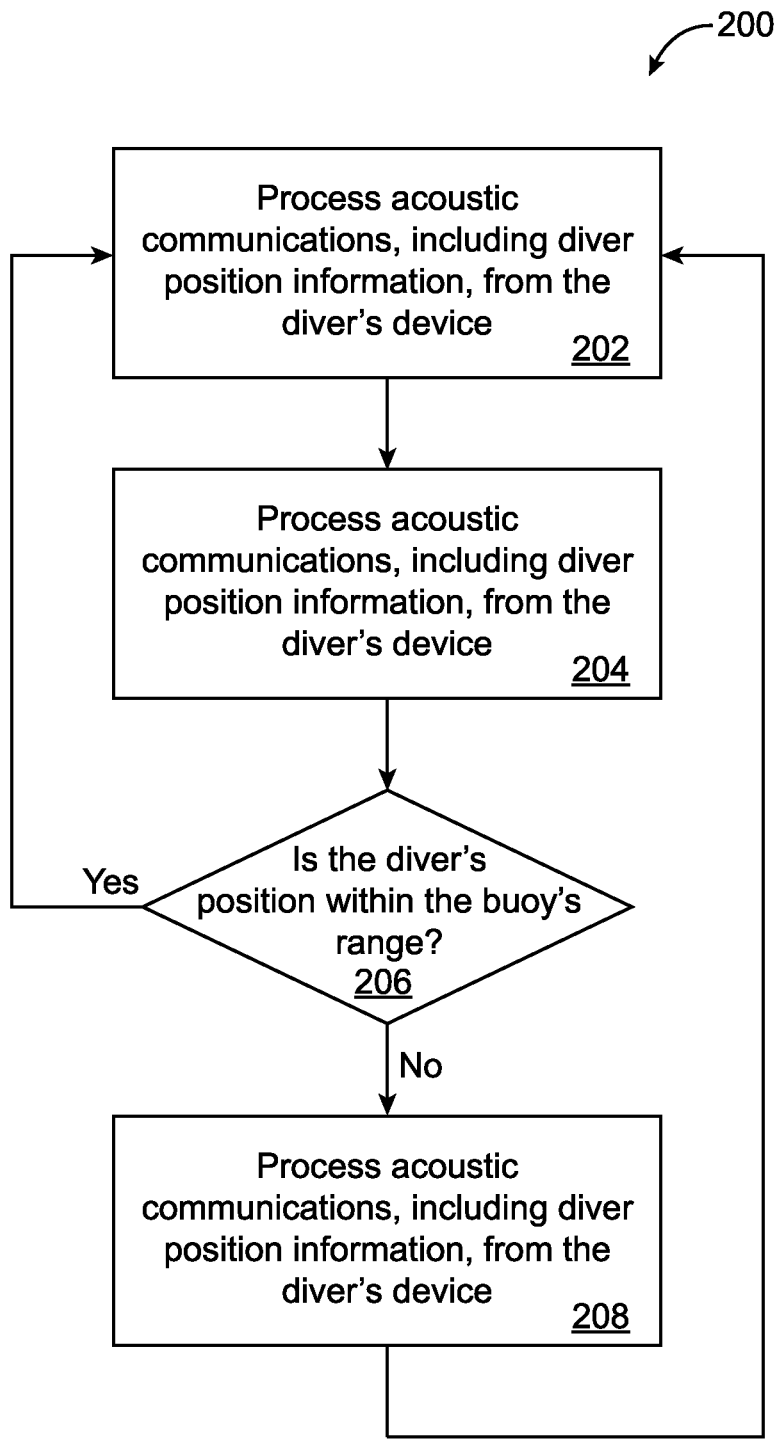
FIG. 2 is a flow chart illustrating operation of an embodiment of a self-propelled buoy.

Referring now to FIGS. 1, 1a and 2, an embodiment of a buoy 100 includes an acoustic communication module 102 that is coupled to a diver monitoring module 104 and a propulsion controller 106. The acoustic communication module 102 is configured to receive acoustic communications from a communication device 90 (sometimes referred to herein as device 90) that is attached to a diver 80 or other underwater object 80 described herein (in these cases, device 90 may be integral or otherwise contained in the object). In some embodiments, the device 90 can be a personal computer (that is configured for underwater use), a dive computer, a dive watch, a smartphone, a personal digital assistant (PDA), a sonar device, or other electronic processing devices.

In one embodiment, the acoustic communication module 102 can be a sonar module that receives acoustic communications sent from the device 90 without the need to establish any sort of link. In another embodiment, before or at the outset of communication between device 90 and acoustic communication module 102, the acoustic communication module 102, first connects or links with the device 90. In particular embodiments, the linkage between module 102 and device 90 can be facilitated by configuring each device 90 to have a unique identification or identifier that is signaled by device 90. In one embodiment, the unique identification is an acoustic signature. Once the device 90 is connected to the buoy 100, the device 90 can transmit acoustic communications to the buoy 100. In addition, in some embodiments, the buoy 100 can connect or link with multiple devices, with each device having its own unique identification. The acoustic communication may be continuous, but more preferably occurs discretely in the form of a pulse or chirp sent by the device 90 attached to the diver. The chirp may be sent at regular intervals, in response to an event (e.g., biometric data from the diver indicating that the diver is in distress) and/or manually by the diver.

According to an embodiment, the acoustic communications received by the acoustic communication module 102 can include a variety of information such as information about the environment surrounding the device 90, position information of a diver, biometric information of the diver, or information about the diver's equipment. According to the embodiment illustrated in FIG. 1, the acoustic communications in this example includes a unique identification 112 of the device 90, position information 114 of the diver, and the diver's biometric information 116. In some embodiments, position information 114 can include the diver's absolute and lateral distance away from the buoy 100 as well as the diver's depth underneath the buoy 100. In other embodiments, position information 114 can include the diver's distance relative to geographical marks or the diver's actual geographic location on the earth (such as the latitude and longitude of the diver). The buoy 100 can use various methods to determine position information 114 of the diver. In some embodiments, the buoy 100 can determine position information 114 using various sonar methods such as time of flight and beam forming including use of phased arrays. In related embodiments, multiple buoys 100 may be used to determine position information 114 of the diver using, for example, triangulation methods.

The device 90 that is connected or linked to the buoy 100 measures and monitors data of the diver and the surrounding environment. For example, in one embodiment, the device 90 is configured to receive biometric information of the diver. In one embodiment, biometric information can include the diver's oxygen saturation level, heart rate, respiration rate or the diver's blood pressure. Furthermore, in certain embodiments, the device 90 comprises a software module to convert the biometric information to an acoustic communication. The acoustic communication can then be transmitted from the device 90 to the acoustic communication module 102, as described above.

The acoustic communication module 102 receives the acoustic communications and relays them to the diver monitoring module 104 and the propulsion controller 106. In one embodiment, the diver monitoring module 104 receives the unique identification 112, position information 114, and the diver's biometric information 116, and uses them to monitor the diver. The diver monitoring module 104 is configured to relay diver status information 118 to a radio frequency (RF) communication module 110. The diver status information 118 can include information such as the unique identification 112, position information 114, and the biometric information 116 of the diver. In some embodiments, the RF communication module 110 is configured to transmit information 110i from the buoy 100 to another buoy 100' or to a monitoring ship 99 (e.g., a dive boat from which the diver departed), and also receive information from another buoy or the monitoring ship. In this way, the RF communication module 110 can transmit diver status information 118 to the monitoring ship for various purposes (such as for monitoring the diver for the diver's safety and health). Furthermore, the RF communication module 110 can also transmit a variety of different information. This information can include information about the buoy 100 and/or its surrounding environment (such as the buoy's location, ocean currents' speed and direction, the water temperature), or data about the diver and/or his or her surrounding environment (such as position information of the diver, biometric information of the diver, water pressure at the depth of the diver, or information about the diver's equipment). Similarly, in another embodiment, the RF communication module 110 is also configured to receive instructions from another buoy or a monitoring ship.

According to another embodiment, the acoustic communication module 102 also receives the acoustic communications and transmits the unique identification 112 and position information 114 to the propulsion controller 106. Furthermore, the propulsion controller 106 is coupled to a propulsion system 108. As discussed above, according to some embodiments, the propulsion system 108 can comprise one or more motors with a combination of propellers, paddle wheels, air fans, or pump jets, or other means for enabling movement in water. For propeller embodiments, the propulsion system can include at least a first propeller and may include a second third, fourth or other selectable number. The motors can be an internal combustion engine, electric motor, or a combination of both. The propulsion controller 106 is configured to receive position information 114 of the diver, and based on the position information 114, determine if the diver is within a predetermined range of the buoy 100. Based on this determination, the propulsion controller 106 outputs control information 122 to the propulsion system 108. Control information 122 can include one or more of speed and the direction of the propulsion system including the direction of propellers, rudder or other steering device used by the propulsion system. This enables the propulsion controller 106 to control the propulsion system 108 in moving the buoy 100 to an effective communication range (herein "effective range" or "pre-determined range") if the diver is outside the predetermined range of the buoy 100. Thus, the propulsion controller 106 can effectively enable the buoy 100 to be in constant effective range with the diver. Therefore, in one embodiment, the buoy 100 is configured to be self-propelled and automatically move to be within the effective range of the diver, also described herein as autonomously controlled. In another embodiment, the buoy 100 can be manually operated by the diver using his or her device, and control the buoy's 100 movement.

In some embodiments, the propulsion controller 106 is coupled to the RF communication module 110 and also receives a global positioning system (GPS) input 124 from a GPS device or other similar navigational devices. Based on the GPS input 124, the propulsion controller 106 transmits buoy location data 120 to the RF communication module 110. The RF communication module 110 can then transmit the buoy location data 120 to another buoy or a monitoring ship for various purposes. GPS signal 124 can also be used by controller 106 for controlling the direction that the buoy is moved by propulsion system 108 including making course corrections and/or refining the direction of travel of the buoy so as to minimize distance and travel time for reaching a desired location within the effective distance. In this and related embodiments, the buoy 100 can also be manually operated by someone on a monitoring ship, so that he or she can control the movement of the buoy 100 remotely.

In other embodiments, the buoy 100 can also communicate with an automated device 80a or other device 80a that responds to human control, such as a robot, remote controlled submarine, or other remote controlled device. The automated device or robot 80*a* also has a unique identification that can enable it to connect to or link to the buoy 100. The buoy 100 can also connect or link to multiple automated devices or robots, with each automated device or robot having its own unique identification. In one embodiment, the unique identification can be an acoustic signature. Like the device 90 attached to a diver, the automated device or robot 80*a* can also be configured to transmit acoustic communications to the buoy 100.

As described above, in one or more embodiments, the buoy 100 comprises an acoustic communication module 102. The acoustic communication module 102 can comprise an acoustic transmitter and receiver 103 to send and receive acoustic communications from a device attached to a diver. In various embodiments, transmitter and receiver 103 can comprise a single acoustic element 103' or separate acoustic elements 103'. In one embodiment, the acoustic communication module 102 can be positioned toward the bottom of the buoy 100, facing towards the ocean floor. In another embodiment, the acoustic transmitter and receiver 103 is stabilized on the buoy 100 through use of a stabilizing device or mechanism 130, such as a multi-axis gimbal or a gyroscope, for example. This allows for the acoustic transmitter and receiver 103 to generally maintain its/their orientation in facing toward the ocean floor despite the buoy's 100 movement due to ocean waves, currents, etc. and movement when the buoy is being propelled by propulsion system 108.

In an additional or other alternative embodiment, acoustic receiver and transmitter 103 can be movable so as to change its orientation, for example, depending on the tilt or other movement of buoy 100. In these and related embodiments, the buoy 100 can also include an accelerometer 105 or other like sensor to sense and determine the motion of the buoy 100 in one or more axis. In use, accelerometer 105 can be used to generate a signal 105*t* for adjusting the direction of the acoustic transmitter and receiver 103 (e.g., depending on the motion of the buoy 100). It may also be used as a signal 105*m* for adjusting movable portions of buoy 100 discussed herein (e.g., such as a movable flange 304*m* shown in FIG. 1*a*) so as to vertically stabilize the buoy during motion from waves or when the buoy is being moved by propulsion system 108.

The buoy 100 can also include a power system 140 for powering one or more components of buoy 100 including propulsion system 108. Power system 140 can correspond to various battery powered electrical systems 140 known in the art. In particular embodiments, the power system 140 can be a regenerative power system 140*r*, such as a solar powered battery system or a wave powered battery system that recharges a stored rechargeable battery automatically. For solar powered embodiments, a solar panel or other solar energy converter can be used to apply a trickle charge or other charging regimen for the particular battery chemistry, e.g., lead acid. In other embodiments, the regenerative power system can include a rechargeable battery that can be manually recharged. Various rechargeable batteries can be used, but in preferred embodiments that battery system is a marine rated lead acid system known in the art.

FIG. 2 is a flow chart illustrating an embodiment of a self-propelled buoy. Flow chart 200 illustrates a method for functionality of the buoy 100 of FIG. 1. First, at step 202, the buoy processes the acoustic communications from the device 90. As described previously, the buoy can connect or link to the device 90 using the device's unique identification. The buoy can also connect to multiple devices, each with its own unique identification. Furthermore, in one embodiment, the unique identification can be an acoustic signature. Referring back to step 202, the acoustic communications can include a diver's position information. In one embodiment, position information can include the diver's lateral distance away from the buoy as well as the diver's depth underneath the buoy. In other embodiments, position information can include the diver's distance relative to geographical marks, or can be the diver's geographic location on the earth (such as the latitude and longitude of the diver).

Once the buoy 100 processes the acoustic communications from the device 90, including the diver's position information, at step 204, the buoy is enabled to control the propulsion system using the diver's position information. The buoy is able to control the propulsion system and move in any direction in the water. In one embodiment, the buoy is self-propelled and moves automatically depending on the acoustic communications it receives. In another embodiment, the buoy can be manually controlled by the diver using the device 90, or by someone monitoring the buoy 100 from a monitoring ship.

At step 206, by using the diver's position information, the buoy makes a determination of whether the diver is within a predetermined range of the buoy or whether the diver is outside the predetermined range. Depending on this determination, the buoy can control the propulsion system to move in different directions. If the diver's position is within the buoy's range, the buoy will continue to process acoustic communications from the device 90, represented by the arrow back to step 202 in FIG. 2. The buoy does not have to move because the diver is within the predetermined range of the buoy. On the other hand, if the diver's position is not within the buoy's range, then the buoy will control the propulsion system in moving the buoy to an effective range, as illustrated in step 208.

A variety of approaches can be used for controlling the propulsion system so as to have the buoy stay within the effective range. In one embodiment, the buoy can control the propulsion system by turning on or off one or more propellers. In other embodiments, the propulsion system can enable the propellers to change positions and face different directions and/or change the direction of a rudder or other steering device used in conjunction with the propeller(s). In another embodiment, the buoy can control the propulsion system 108 by making one or more propellers turn faster than another to enable the buoy to move faster in one direction than another. This enables the buoy to quickly move to an effective range if the diver is rapidly moving away from the buoy's range. In still another embodiment, the movable portions 304*m* of a flange 304 can be used for one or more of steering, propulsion or stabilization of the buoy. At step 208, once the buoy controls the propulsion system in moving the buoy to an effective range, the buoy will continue to process acoustic communications from the diver's device at step 202. These steps can continually repeat to enable the buoy to always remain in an effective range of the diver. In some embodiments, these steps can be adapted to move the buoy within a predetermined pattern, such as a circle or oval so as to stay within the effective range. The particular pattern and its parameters (e.g., shape, dimensions, speed, etc.) can be stored as a pattern algorithm 109 in controller 106 either directly or indirectly via memory resources 107 coupled to the controller). Entry into the pattern movement mode and a particular pattern can be selected depending upon one or more factors such as the direction and speed of waves and ocean currents and the direction and speed of the diver's movements. For example, an oval pattern can be used when there is an ocean current pushing the diver or the buoy away from one another so that the short end of the oval is used when the buoy is down current from the diver. Various numerical methods/algorithms (e.g., least squares, Newton-Raphson method, Euler methods, cubit spline, etc.) can be employed to optimize pattern shape and dimensions so as more easily stay within the effective range with reduced amounts of correction by propulsion system 108. These same methods can also employed when the buoy is only moving in a linear fashion with course corrections to account for changes in diver movement and ocean currents, etc. Various embodiments of the pattern movement mode can also be used in cases where the buoy temporarily loses track of the diver's position, so that the buoy moves in a circle or other pattern about the diver's last known position so as to facilitate re-acquisition of the diver's position and re-establishment of communication with device 90. In one or more embodiments this can be facilitated by moving in circle or other pattern to keep the acoustic transmitter and receiver device 103 pointed in the direction of the diver's last known position with possible adjustments for waves, ocean currents, and the diver's last known movements. Based on one or more factors (e.g., the diver's last known position, ocean currents, etc.), the shape of the pattern can be specifically calculated to increase the probability of re-acquiring the diver's position and re-establishing communication. Again, various numerical methods (e.g., Newton Raphson, Euler, etc.) can be used to generate and update the pattern. Such a pattern, such as circle, oval, etc. can also be used to keep the acoustic transmitter and receiver device 103 pointed in a direction where the diver is likely to be even when the diver's current position is not known. Also, when the buoy loses contact with the diver, acoustic communication module 102 can send out a unique reacquisition signal which is higher strength and likely to have longer effective ranges so as to make contact with re-establish communications with the diver's communication device 90 (or that of another underwater object described herein).

In additional or alternative embodiments, various embodiments of buoy 100 including propulsion controller 106 may also include a power savings mode whereby controller 106 is configured to maintain the buoy within the effective range using minimal power consumption by propulsion system 108. Several approaches can be used for such a lower power savings mode and they can be stored as algorithms 111 in controller 106 or memory resources 107. In one approach, the propulsion system 108 only comes on when buoy 100 is at or near the effective range. When it does come on, the propulsion system may stay on to maneuver the buoy 100 to a selectable distance from the diver so as to be inside the effective range. That selectable distance may be just inside the effective range or may be a closer distance calculated to minimize the time when the propulsion system has to come on again based on one or more of the speed and direction of ocean or other current and movement of the diver. Various optimization methods, such as linear optimization or non-linear optimization, may be used to calculate the optimal distance the buoy should be kept from the diver so as to minimize power consumption depending upon ocean one or more of currents, diver movement and other parameters. In another approach for a power savings mode, the propulsion system comes on a fixed time intervals (e.g., every 10 minutes) and stays on till it gets the buoy back into the effective range or a selected closer distance. Buoy 100 can be put into a selected power savings mode by a signal from the diver or other underwater object or the dive boat. It may also automatically go into the power savings mode when the charge of its battery power supply falls below a threshold level (e.g., as determined by voltage, or current) or during or during non-daylight conditions (e.g., nightfall or during extended cloudy periods) when the ability to recharge the battery is diminished.

In addition to self-propelled autonomously controlled embodiments of the buoy 100, other embodiments of the invention can provide a manually controlled buoy 100 which can be controlled, for example, by the diver or by a person monitoring the diver and the buoy aboard a monitoring ship. In addition, in other embodiments, the propulsion system can use different means and methods of movement as discussed previously.

Figure 1B:
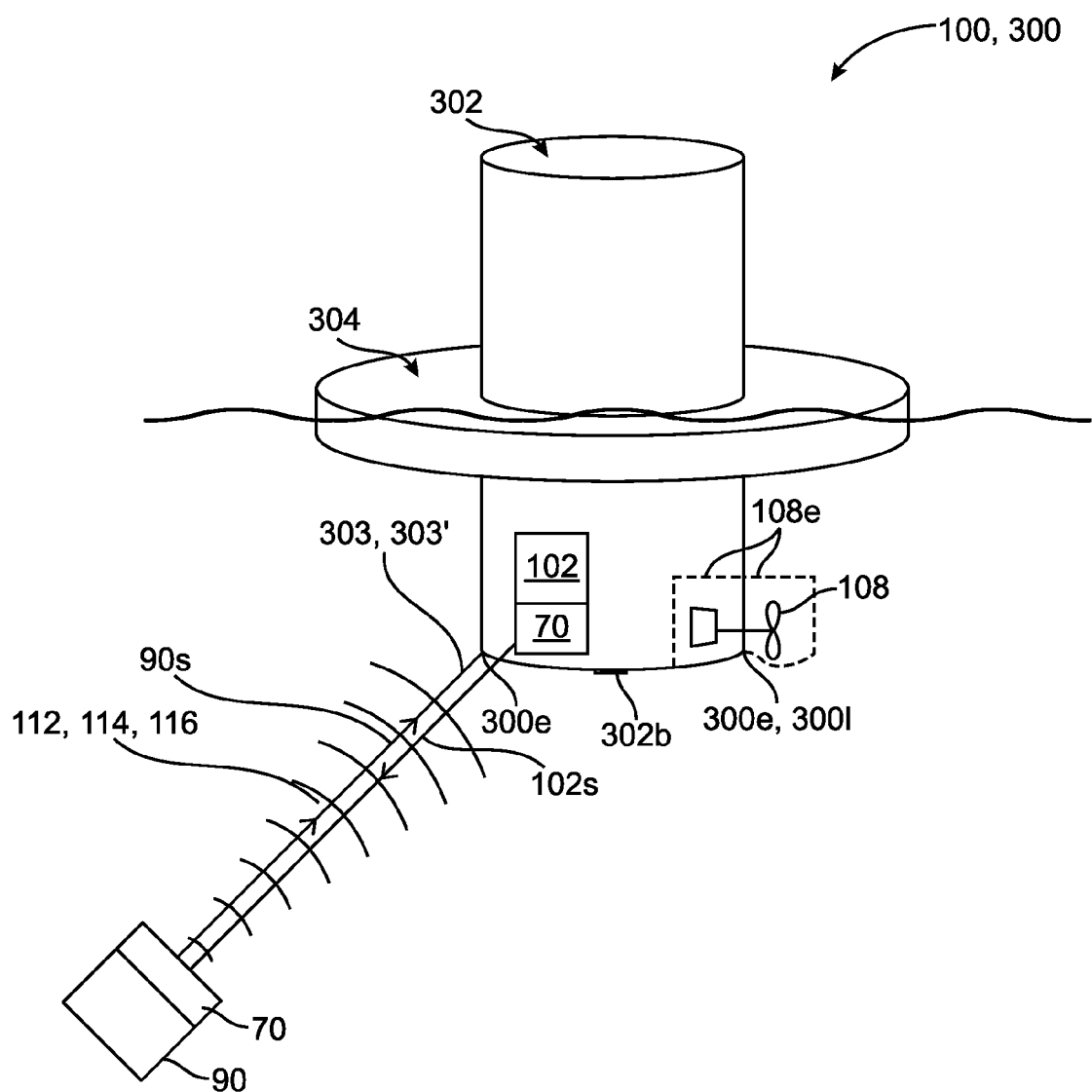
FIG. 1b illustrates an embodiment of a self-propelled buoy configured to reduce acoustic interference from its propulsion system and other sources.
Figure 3:
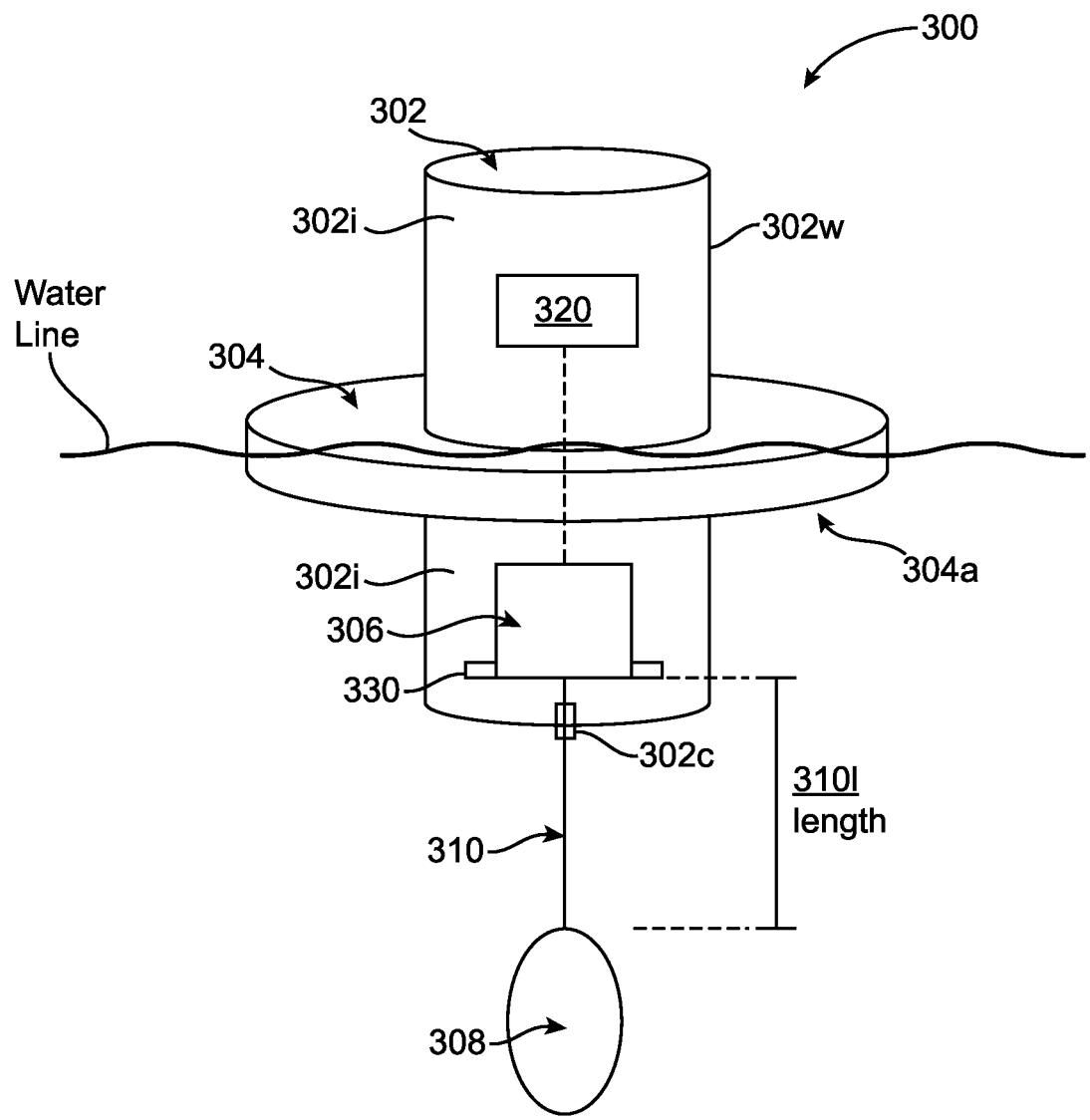
FIG. 3 illustrates an embodiment of a buoy as part of a power generation system.

Referring now to FIGS. 1a, 1b and 3, a description will now be presented of some of the structural and related components of embodiments of buoy 100, 300. The buoy 300 comprises a body portion 302, a flange or other water surface contact feature 304 coupled to the body portion, an energy converter 306, and an inertial weight 308. Although the example in FIG. 1a illustrates the body portion 302 as a cylindrical shape, the body portion 302 can be designed in various shapes, such as rectangular, circular, conical, etc. In many embodiments, the body portion 302 can also provide housing for a plurality of the devices described in FIGS. 1, 1a and 3. The bottom or below the water portion 302b of body portion 302 can also have a variety of shapes which can be configured for both stability of the buoy when it is stationary as well as reduced drag when it is being propelled. Accordingly, in various embodiments, bottom portion 302b can have a v, rounded v shape or like shape to allow for both static stability and reduced drag when it is being moved through water by propulsion system 108. In one particular embodiment, bottom portion 302b can be configured to modify its have from a round like shape when static for improve static stability and to a v like or conical shape when moving for reduced drag. Such modifiable bottom portions 302b can be achieved through the use of various shape memory materials known in the art, or slide-able rounded panels (not shown) which can be retracted into body portion 302 when propulsion system 108 is engaged. In other embodiment, portion 302b can be configured to have a round like shape but can include deployable hydrofoils (not shown) which are deployed when propulsion system 108 is engaged so as to allow at least a portion of bottom portion 302b come out of the water. Preferably, in these and related embodiments, acoustic transmitter and receiver 103 is deployed into the water and or towed behind body 302 so as to allow it to remain beneath the water so send and receive acoustic communications with device 90 while the buoy is moving.

Flange portion 304 can be configured to perform a variety of functions. These can include for example, helping the buoy to float, stabilizing the buoy including vertically stabilizing the buoy, sensing wave motion, and assisting with a power generation function as described below. In particular embodiments, the flange 304 can function as a stabilizing element 304' configured to vertically stabilize the buoy from rocking or other motion resulting waves or when the buoy is propelling itself through the water. The amount of stabilization is sufficient to keep acoustic receiver and transmitter 103 (or a component thereof, e.g., acoustic element 103') of acoustic communication module 102 submerged in the water during waves and/or when the buoy is being propelled or both. In use, such configurations of flange 304 allow buoy 300 to maintain communication with communication device 90 as to be able to continue to monitor the diver 80 and/or obtain position information 114 on the diver when the buoy is being rocked or otherwise moved by waves or from propulsion.

The flange 304 can also be designed in various shapes, such as rectangular, circular, conical, etc. It is positioned on the body portion 302 to enable the flange portion 304 to float on the surface of the water. It may be integral with or attached to the body portion 302 either directly (e.g., via a weld) or via an attachment means including a pivoting or other movable attachment means 303 such as a movable bracket, universal joint, ball and socket joint and like components. For embodiments, having a movable flange 304, the flange 304 can be configured to sense various characteristics of wave motions including height, frequency, etc. This can be achieved by the use of one more accelerometers or other motion or related sensor 304s, positioned on the flange. In some embodiments, flange 304 can include a movable portion 304m, also attached by a movable attachment means 303. Movable portion 304m can be configured to perform one or more of the following functions: i) steerage of the buoy (as an adjunct to or in conjunction with propulsion system 108), ii) stabilize buoy on the water surface; iii) propulsion of the buoy particularly for maneuvering, iv) sense wave characteristics including, velocity, frequency, height, etc.; and v) power generation. Movable portion 304m may be servo-controlled for performing one or more of these functions. In particular embodiments, movable portion 304m can be servo or otherwise controlled in response to a signal from accelerometer or other sensor so as to vertically stabilize the buoy during waves or when the buoy is being moved by propulsion system 108.

Figure 1C:
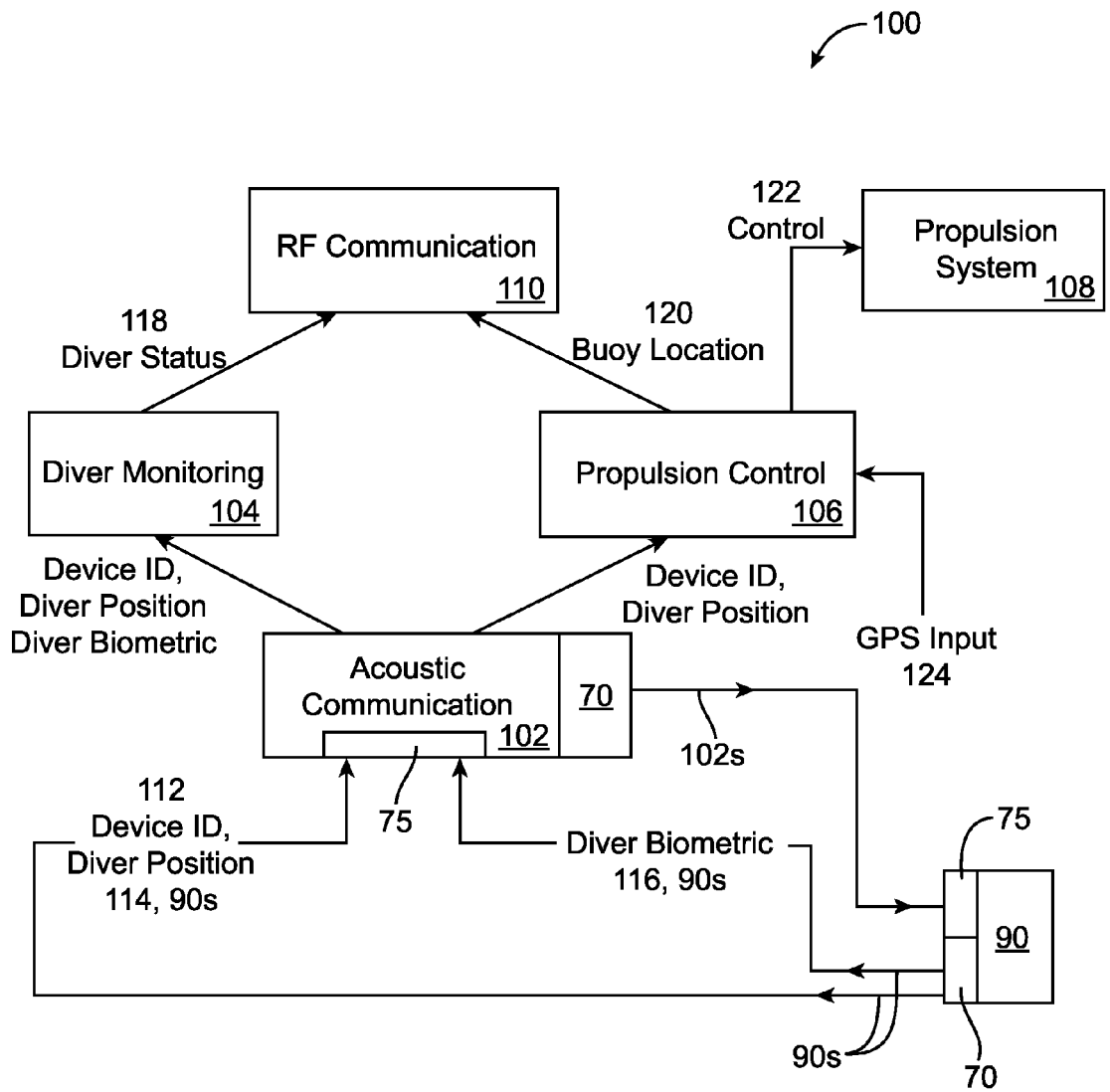
FIG. 1c is a block diagram illustrating the components of an embodiment of a self-propelled buoy configured to reduce acoustic interference from its propulsion system and other sources.

Referring now to FIGS. 1b and 1c, a description will now be presented for various approaches for reducing or otherwise compensating for any acoustic (or other) interference from propulsion system 108 with acoustic communications between device 90 and acoustic communications module 102. One or more of these embodiments may be used to allow communications between the buoy 100 and device 90 while the buoy is moving under power from propulsion system 108 (or by another propulsion means such as a tow line from a boat) or is being moved by ocean waves or currents. Further such embodiments allow substantially unhindered communication of one or more of signals 90s including signals 112, 114, 116 to acoustic communication module 102 while under such conditions. In one or more embodiments, such reduction or compensation can be achieved by placing propulsion system 108 as far away as possible from acoustic transmitter and receiver 303, for example on an opposite (e.g., diametrically opposite) locations 300l of buoy 300, such as opposite ends 300e. Additionally propulsion system 108 may be placed in a structure 108e arranged and configured to acoustically isolate propulsion system 108 or otherwise acoustically dampen sound from system 108. Structure 108e can enclose all or a portion of propulsion system 108 and can comprise various acoustically insulating materials known in the art including various marine-based acoustically insulating materials. In particular embodiments, structure 108e is configured to acoustically dampen or eliminate cavitation sounds and other noise from a propeller based propulsion system 108. In other embodiments, one or more of the signals 90s, received from device 90, (e.g., 112, 114 and 116) can be processed so as to reduce or prevent acoustic interference. In one approach, signals 90s can either be frequency shifted to a higher or lower frequency than that from the acoustic interference from system 108. In another approach signals 90 can be frequency modulated to a higher or lower frequency than that of the acoustic interference such the acoustic interference has minimal effect of the fidelity of signal 90s. In still another approach, the amplitude of signal 90s can be selected to far exceed that of the acoustic interference so again there is minimal effect on the fidelity of signal 90s (e.g., due to high signal to noise ratios). One or more of these approaches can also be used for signals 102s generated from module 102. In these and related embodiments such signal processing can be done by a signal processing device or devices 70 known in the art (which can be either analogue (including one or more circuits), digital or both). Similar such processing devices 70 can also be incorporated into device 90. In still another approach for reducing acoustic interference from system 108, in various embodiments, acoustic module 102 can include a filter 75 having a band-pass selected to admit signals 90s and filter out the frequency range of the acoustic interference of the particular propulsion system 108 (e.g., a propeller based system). Filter 75 can also be incorporated into device 90 and can be selected from various band-pass filters known in the art.

Figure 4:
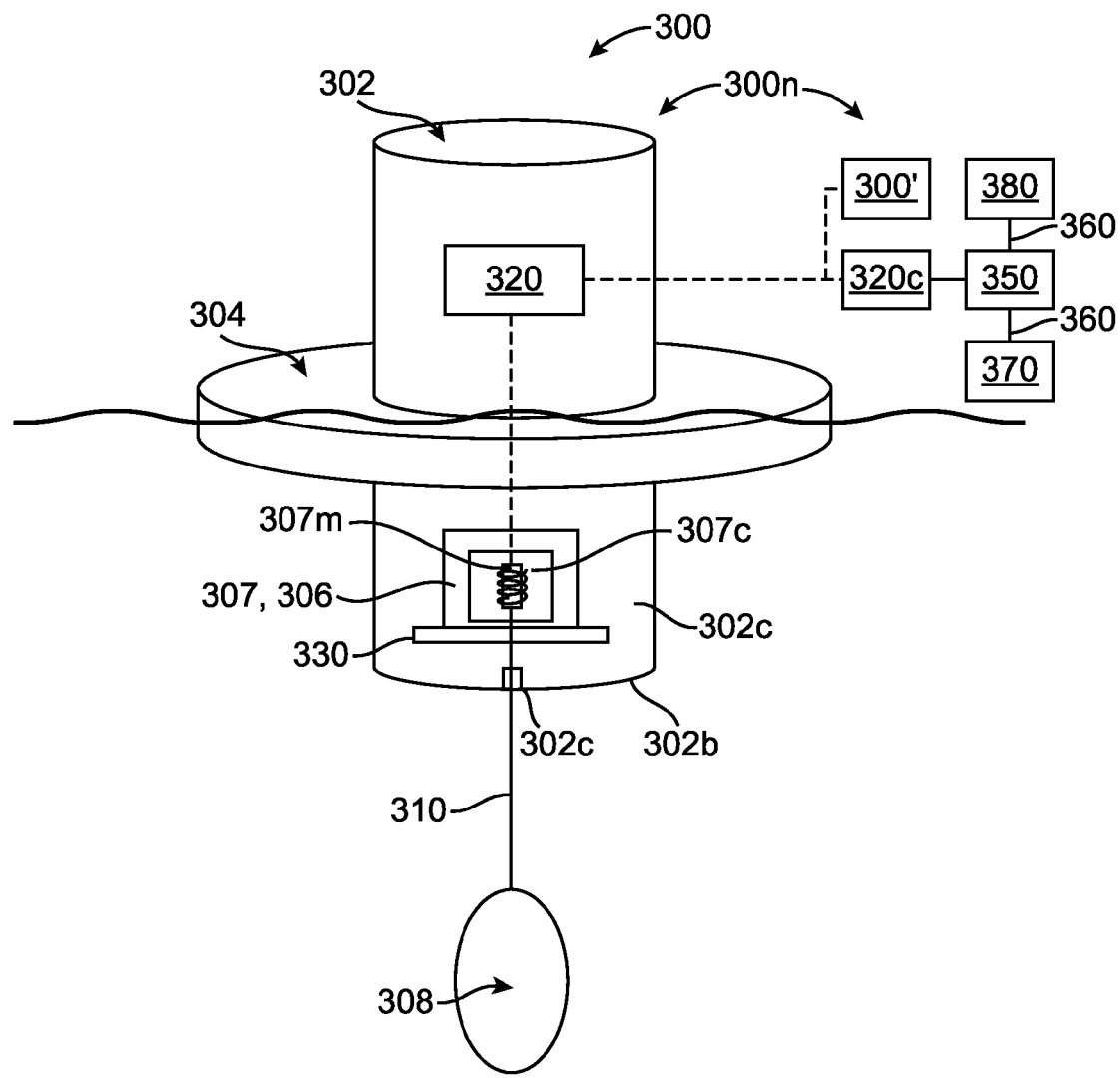
FIG. 4 illustrates an embodiment of a power generating buoy having a magnetic based energy generator.

Referring now to FIGS. 3 and 4, in various embodiments, buoy 300 can be configured to generate energy from waves, tides and other motion in the ocean or other body of water in which it is floating. Accordingly, in these and related embodiments, buoy 300 can include an energy converter 306 and an inertial weight 308. In these embodiments the buoy includes a body portion 302 having a wall 302w (which is constructed to be water tight) and interior volume 302i which may contain one or more components of buoy 300 so as to shield them from the elements. For example, energy converter 306 is preferably positioned in an interior volume 302i (but also may be placed externally). The energy converter 306 and the inertial weight 308 are connected by a cable or other connection means 310 (e.g., a shaft, chain, gear, cam, etc.) which may extend through a water tight conduit 302c in wall 302w. The buoy 300 is configured to have sufficient buoyancy to float on the water with inertial weight 306 attached. The selected amount of buoyancy can also be achieved through the use of an attached flange 304, which has a selected amount of water contacting surface area 304a to provide the necessary amount of buoyancy. Because the buoy 300 floats on or near the surface of the water, it will move up and down with the movement of the ocean waves. As the buoy 300 moves up, for example, the inertial weight 308 exerts a force in a downward direction, towards the ocean floor. As the inertial weight 308 exerts force in the downward direction, it pulls the cable 310 down causing a transfer of energy in the energy converter 306. In various embodiments flange 304 also is configured to provide vertical stability as described herein so as to reduce any rocking motion of the buoy during a wave which may interfere with the vertical motion of weight 308 and cable 310 (e.g., by causing a pendulum like motion). In specific embodiments, the water contacting surface area 304a of flange 304 is sufficient to dampen out or otherwise minimize any such pendulum like motion.

In one or more embodiments, energy converter 306 can correspond to an electric generator 306 that can generate electrical current in response to the energy transfer by the inertial weight 308. In various embodiments, electric generator 306 can comprise an AC or DC generator 306. The generator (either AC or DC), is a marine-rated generator configured to tolerate marine conditions. The selection of generator 306 (as well as weight 308 and cable 310) can also be tailored to the particular wave characteristics where the buoy 300 is placed including frequency, so as achieve optimal power generation. Also, in one or more embodiments, the generator 306 may be mounted on a gimbal or other motion dampening or stabilization means 330 so as to minimize any motion of the buoy (e.g., wave motion) which could impede or impair energy generation.

In an embodiment shown in FIG. 4, the energy converter 306 can comprise a magnetic based generator 307 having a magnetic core 307m, positioned within a coil, 307c wherein displacement of the core by force from the counter generates the electric power signal. The magnetic force of the core may be matched to the mass of counterweight 308 (e.g., by an integer like value) based and to improve the efficiency of energy conversion. Also the resonant frequency of the combination of the core 307m, the counterweight 308 and coil 307c may be matched to a frequency of ocean waves to improve the efficiency of energy conversion.

In one or more embodiments of an energy generating buoy 300, the buoy also includes an internal power storage device 320 to store the energy acquired by the energy converter 306. In another embodiment, the buoy's 300 internal power storage 320 can be linked by an electrical cable 340 to another buoy 300' or to a central power storage device 320c. This enables the central power storage to receive the power generated by the buoy 300. The power generation system can also include multiple buoys 300 that are interconnected together in a power generating network 300n of buoys 300. The network 300n of buoys 300 can also be connected to the central power storage 320c. In another embodiment, the central power storage 320c is also coupled to a transformer 350 to allow for a step up or step down in voltage that is generated for example, for power transmission. Cables 360 connected to the transformer 350 can transfer the power to an onshore power station 370 or to a ship 380, for example.

In another embodiment, the surface area of the flange 304, the weight of the inertial weight 308, and the length of the cable 310 are selected to enable the buoy 300 to float on or near the surface of the water. This enables the buoy 300 to remain on or near the surface of the water so that the inertial weight 308 can move in a downward direction without sinking the buoy 300. In still other embodiments, the surface area of the flange 304, the mass of the inertial weight 308, and the length 310l of the cable 310 can be selected to correlate with a frequency of ocean waves or other wave characteristic (e.g., amplitude) so as to maximize or otherwise increase energy generation. The correlation to ocean wave frequency can be proportional, linear or non-linear (e.g., geometric, logarithmic, second order, etc.). Also, in some embodiments the length of cable or other connecting means 310 can be adjustable (e.g., shortened or lengthened), for example in response to changes in ocean wave frequency, in order to maintain a desired correlation to that frequency. In related embodiments, the length 310l of cable 310 can be adjusted to another parameter, such as wave height, wave width, wave shape (smooth, vs. breaking or wind-blown) and buoy dimensions (e.g., length and width), In other embodiments, the buoy 300 does not include a flange 304. In these embodiments, buoy 300 can be shaped in a way that enables the buoy 300 to float on or near the surface of the water by itself. In another embodiment, the buoy 300 can include the features of the buoy 100 as described in FIG. 1 and be self-propelled.

Conclusion

Although illustrative embodiments of the invention have been described in detail herein with reference to the accompanying drawings, it is to be understood that the invention is not limited to those precise embodiments. As such, many modifications and variations will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mentioned of the particular feature. This, the absence of describing combinations should not preclude the inventor from claiming rights to such combinations.

What is claimed is:

1. A self-propelled buoy for communication with an underwater object, the buoy comprising:
   a propulsion system for propelling the buoy;
   an acoustic communication module configured to at least receive acoustic communications from a communication device associated with the underwater object; and
   a propulsion controller that identifies, from the acoustic communications received by the acoustic communication module, position information for the communication device associated with the underwater object, wherein the propulsion controller outputs control information to control the propulsion system of the buoy to stay within a selected distance of the underwater object, and wherein the propulsion controller includes a course correction algorithm for making course corrections of the buoy which account for at least one of changes in underwater currents or in a movement of the underwater object, the course corrections enabling the buoy to stay within the selected distance of the underwater object.

2. The buoy of claim 1, wherein the communication device is attached to the underwater object.

3. The buoy of claim 1, wherein the propulsion system comprises a propeller driven system including at least one propeller.

4. The buoy of claim 1, wherein the propulsion system comprises an internal combustion engine.

5. The buoy of claim 1, wherein the propulsion system comprises an electric motor.

6. The buoy of claim 1, wherein the propulsion controller comprises at least one of a microprocessor, a processor running a software program, a state machine, an analog controller, or a servo controller.

7. The buoy of claim 1, wherein the selected distance is an effective communication range between the communication device and the acoustic communication module.

8. The buoy of claim 1, wherein the acoustic communication module is configured to process sonar communications.

9. The buoy of claim 1, wherein the acoustic communication module is further configured to transmit acoustic communications.

10. The buoy of claim 1, wherein the acoustic communication module establishes a link with the communication device.

11. The buoy of claim 10, wherein the acoustic communication module is configured to detect identification information transmitted by the communication device, and wherein the identification information is processed by the acoustic communication module to establish the link.

12. The buoy of claim 11, wherein the identification information comprises an acoustic signature unique to the communication device.

13. The buoy of claim 1, wherein the position information comprise at least one of a latitude and longitude of the underwater object, a depth of the underwater object in a body of water beneath the buoy, an absolute distance between the underwater object and the buoy, a velocity of the underwater object, or a velocity of the buoy.

14. The buoy of claim 1, wherein the buoy includes signal processing means for processing the acoustic communications to reduce acoustic interference from the propulsion system to allow the acoustic communication module to communicate with the communication device when the propulsion system is on.

15. The buoy of claim 14, wherein the signal processing means comprise at least one of a signal processing device, an analog signal processing device or a digital signal processing device.

16. The buoy of claim 14, wherein the signal processing means comprises a filter for filtering out interference from the propulsion system.

17. The buoy of claim 16 wherein the filter comprises an analog filter, a digital filter or a band-pass filter.

18. The buoy of claim 14 wherein the signal processing means allows the acoustic communication module to send and receive communications when the propulsion system is on.

19. The buoy of claim 14, wherein the processing by the signal processing means comprises modulation, frequency modulation, or frequency shifting of the acoustic communication.

20. The buoy of claim 14, wherein the signal processing means allows the propulsion controller to obtain position information from the acoustic communication while the propulsion system is on.

21. The buoy of claim 14, wherein the propulsion system includes a propeller, and wherein the acoustic communication module is configured to process the communication to reduce interference from the propeller, the interference including cavitation sounds from the propeller.

22. The buoy of claim 1, wherein the propulsion system is arranged and configured to reduce acoustic interference from the propulsion system to allow the acoustic communication module to communicate with the communication device when the propulsion system is on.

23. The buoy of claim 22, wherein the acoustic module includes an acoustic receiving or transceiving element and the propulsion system is positioned on a diametrically opposite location on the buoy as the acoustic receiving or transceiving element.

24. The buoy of claim 22, further comprising an acoustically insulating structure partially disposed about the propulsion system such that the propulsion system is at least partially acoustically insulated from the acoustic communication module.

25. The buoy of claim 1 wherein the underwater object is a diver and the communication device is carried or worn by the diver.

26. The buoy of claim 25, wherein the acoustic communications include biometric information relating to the diver.

27. The buoy of claim 26, wherein the biometric information comprises at least one of a blood oxygen saturation or a blood nitrogen saturation.

28. The buoy of claim 2, wherein the acoustic communication module comprises at least one acoustic element positioned in the water for receiving or transceiving the acoustic communications.

29. The buoy of claim 28, wherein the at least one acoustic element is operably coupled to a stabilization device to maintain an orientation of the acoustic element in the water for communication with the communication device as the buoy moves through water.

30. The buoy of claim 29, wherein stabilization device comprises at least one of a gimbal or a gyroscope.

31. The buoy of claim 1, further comprising a stabilization element coupled to a body portion of the buoy for vertically stabilizing the buoy.

32. The buoy of claim 31, wherein the stabilization element comprises at least one of a flange or a buoyant flange.

33. The buoy of claim 31, wherein the buoy includes an accelerometer for sensing movement of the buoy in at least one axis.

34. The buoy of claim 33, wherein a signal from the accelerometer is used by the stabilization element to vertically stabilize the buoy.

35. The buoy of claim 1, wherein the propulsion controller includes a power savings mode for conserving power expended while moving the buoy to stay within the selected distance of the underwater object.

36. The buoy of claim 1, further comprising a radio frequency (RF) communication module for communicating information between the buoy and another buoy or a monitoring ship, the RF communication module coupled to at least one of the acoustic communication module or the propulsion controller.

37. The buoy of claim 1, wherein the propulsion controller receives an input from a GPS device for controlling a direction of travel of the buoy or for transmission to another buoy or monitoring ship.

* * * * *